| United States Patent [19] | [11] | 4,107,090 |
|---|---|---|
| Fasman et al. | [45] | Aug. 15, 1978 |

[54] CATALYST FOR HYDROGENOLYSIS OF N,N-DIMETHYL-3,5-DITERT.BUTYL-4-HYDROXYBENZYLAMINE

[76] Inventors: Anatoly Borisovich Fasman, ulitsa Kazachya, 3"a"; Dmitry Vladimirovich Sokolsky, ulitsa Kalinina, 71, kv. 4, both of Alma-Ata; Grigory Iosifovich Rutman, ulitsa Revoljutsionnaya, 7, kv. 6; Jury Ivanovich Michurov, prospekt Lenina, 13, kv. 4, both of Sterlitamak, Bashkirskaya ASSR; Viktor Anatolievich Zavorin, 2 Vesnovskaya ulitsa, 45, kv. 88, Alma-Ata; Zoya Stepanovna Shalimova, ulitsa Druzhby, 19, kv. 56, Sterlitamak, Bashkirskaya ASSR; Venera Fatykhovna Timofeeva, ulitsa Zharokova, 184, kv. 5, Alma-Ata; Tulkibai Galikbarovich Dautov, ulitsa I.Nasyri, 13, kv. 96, Sterlitamak, Bashkirskaya ASSR; Daniel Kalimullovich Bazhakov, ulitsa Satpaeva, 37, kv. 41, Alma-Ata; Jury Mikhailovich Sivakov, ulitsa Dybenko, 22, korpus 5, kv. 385, Moscow, all of U.S.S.R.

[21] Appl. No.: 807,254

[22] Filed: Jun. 16, 1977

[30] Foreign Application Priority Data

Jun. 21, 1976 [SU] U.S.S.R. .............................. 2374525

[51] Int. Cl.$^2$ .................... B01J 21/04; B01J 23/64; B01J 23/86; B01J 23/88
[52] U.S. Cl. .................................... 252/465; 568/716
[58] Field of Search .......................... 252/465; 75/138; 260/621 M

[56] References Cited

U.S. PATENT DOCUMENTS 3,919,332  11/1975  Wollensack .................... 260/621 M

*Primary Examiner*—W. J. Shine
*Attorney, Agent, or Firm*—Lackenbach, Lilling & Siegel

[57] ABSTRACT

A catalyst for hydrogenolysis of N,N-dimethyl-3,5-ditert.butyl-4-hydroxybenzylamine which comprises an alloy of nickel, aluminum, chromium, molybdenum and palladium. The components are contained in said alloy in the following proportions, percent by weight:
nickel — 39.0 to 47.7;
chromium — 0.3 to 2.0;
molybdenum — 0.5 to 4.0;
palladium — 0.01 to 0.20;
aluminum — the balance.

The catalyst for hydrogenolysis of N,N-dimethyl-3,5-ditert.butyl-4-hydroxybenzylamine according to the present invention makes it possible to reduce the process duration and lower the content of impurities of stilbenequinone in the final product of the hydrogenolysis (agidol).

1 Claim, No Drawings

CATALYST FOR HYDROGENOLYSIS OF N,N-DIMETHYL-3,5-DITERT.BUTYL-4-HYDROXYBENZYLAMINE

The present invention relates to catalysts employed in hydrogenolysis of substituted aromatic compounds and, more specifically, to a catalyst for hydrogenolysis of N,N-dimethyl-3,5-ditert.butyl-4-hydroxybenzylamine to 2,6-ditert.butyl-4-methylphenol (agidol).

FIELD OF THE INVENTION

The catalyst is useful in the process for producing agidol which is employed as a stabilizing agent for fuels, oils and food products.

BACKGROUND OF THE INVENTION

As catalysts for the process of hydrogenolysis use of N,N-dimethyl-3,5-ditert.butyl-4-hydroxybenzylamine is made of such known catalysts as Ni-Cu/Al$_2$O$_3$, Pd/Al$_2$O$_3$, Pt/Al$_2$O$_3$, Pd/C, Ni deposited on kieselguhr, and a catalyst based on a nickel-aluminum alloy doped with titanium in an amount of from 1 to 8% by weight.

A nickel-aluminum alloy catalyst with a dope of titanium has proven to be the most proper among the prior art catalysts for the reaction of hydrogenolysis for a long run, and possesses sufficient selectivity. The desired product yield, upon performing the process with said catalyst, is as high as 98–99% by weight. However, the presence of 1–2% by weight of an impurity, i.e. stilbenequinone imparts to the desired product a yellow color which requires a double recrystallization, thereby the complicating process.

Furthermore, the catalyst is insufficiently active. Thus, at a temperature of 120° C N,N-dimethyl-3,5-ditert.butyl-4-hydroxybenzylamine is completely converted within 3 hours.

For this reason, catalysts based on the alloy of NiAl$_3$ with an additive of molybdenum and those with an additive of chromium (Ni 46–48% by weight, Cr 2–5% by weight, Al the balance) have been introduced in the art for the process of hydrogenolysis of N,N-dimethyl-3,5-ditert.butyl-4-hydroxybenzylamine.

With the use of said catalysts, the reaction duration at a temperature of 120° C is 2 hours; productivity is increased by 30%, the content of stilbenequinone in the reaction mixture is reduced to 0.1–0.2% by weight; and the desired product acquires no yellow tint upon storage for one year. Output of the desired product is 67 ton/ton of the catalyst.

To eliminate the side reactions resulting in the formation of stilbenequinone, it is necessary to reduce the time of contact of N,N-dimethyl-3,5-ditert.butyl-4-hydroxybenzylamine and agidol with the catalyst; however, the catalyst activity cannot be increased by increasing the hydrogenolysis temperature, since this results in a noticeable resin-formation.

BRIEF DESCRIPTION OF THE INVENTION

It is an object of the present invention to provide a catalyst possessing an increased activity in the reaction of hydrogenolysis of N,N-dimethyl-3,5-ditert.butyl-4-hydroxybenzylamine to agidol and making it possible to perform the process with a minimal formation of agidol.

This object is accomplished by a catalyst for hydrogenolysis of N,N-dimethyl-3,5-ditert.butyl-4-hydroxybenzylamine comprising an alloy based on nickel, aluminum and chromium, in accordance with the present invention, also incorporates molybdenum and palladium, the components being present in the alloy in the following proportions, percent by weight:
- nickel — 39.0 to 47.7;
- chromium — 0.3 to 2.0;
- molybdenum — 0.5 to 4.0;
- palladium — 0.01 to 0.20;
- aluminum — the balance.

DETAILED DESCRIPTION OF THE INVENTION

The present invention is embodied in the following manner.

Into a crucible of an induction smelting furnace aluminum is charged (46.1 to 60.2% by weight) in the form of lumps of any shape. A voltage is applied on the inductor to completely melt aluminum and heat the resulting melt to a temperature within the range of from 1,000 to 1,100° C. Thereafter, nickel is gradually added (39.0 to 47.7% by weight) under agitation. Due to the exothermal reaction of aluminum with nickel, the melt temperature is increased to 1,800° to 2,000° C. Into the same melt, molybdenum is charged (0.5 to 4.0% by weight), along with chromium (0.3 to 2.0% by weight) and palladium (0.01 to 0.20% by weight). Where metallic palladium is used in the form of a finely divided powder, it is wrapped in an aluminum foil prior to the charge. After a complete dissolution of the metals, the melt is agitated, slag is removed and, after cooling to a temperature of 1600° C, the melt is cast into molds.

The cooled ingots are crushed and a required fraction is separated by screening.

Activity of the catalyst according to the present invention is 1.2–2.0 times higher than that of the prior art catalysts employed for hydrogenolysis of N,N-dimethyl-3,5-ditert.butyl-4-hydroxybenzylamine.

The catalyst according to the present invention makes it possible to reduce the content of stilbenequinone in the desired product by 1.7 to 3.3 times.

For a better understanding of the present invention the following examples illustrating its embodiment are given hereinbelow.

EXAMPLE 1

Into an inductor of a high-frequency smelting furnace 560.0 g of aluminum in a graphite crucible are charged. Aluminum is melted and the melt temperature is elevated to 1,000° – 1,100° C. Thereafter, 396.0 g of nickel are gradually added into the molten aluminum under mechanical agitation. After elevation of the melt temperature to 1,800° – 2,000° C into the crucible there are carefully charged under agitation 40.0 g of molybdenum, 3.0 g of chromium and 1.00 g of palladium. After dissolution of the metals, voltage is applied to the inductor for 5 minutes and then switched-off; the melt is agitated and, upon cooling to a temperature of 1,600° C, it is cast from the crucible into an iron mold.

The resulting light-gray uniform alloy has the following composition, percent by weight: Ni 39.6; Cr 0.3; Mo 4.0; Pd 0.1; Al 56.0.

The activity of the catalyst of this alloy in the reaction of hydrogenolysis of N,N-dimethyl-3,5-ditert.butyl-4-hydroxybenzylamine is 1.2–1.6 times as high as that of the catalysts based on Ni-Al-Mo and Ni-Al-Cr alloys.

EXAMPLE 2

Into an inductor of a furnace there is placed 560 g of aluminum in a graphite crucible. Following the procedure described in the foregoing Example 1, charged into the furnaces successively are 390 g of nickel, 40.0 g of molybdenum, 10.0 g of chromium and 0.30 g of palladium.

The resulting alloy has the following composition, percent by weight: 39.0 of Ni, 4.0 of Mo, 1.0 of Cr, 0.03 of Pd, and 56.0 of Al.

The catalyst made of this alloy is by 1.4–2.0 times more active than the catalysts produced from alloys Ni-Al-Mo and Ni-Al-Cr.

EXAMPLE 3

Into an inductor of a furnace there are placed 500.0 g of aluminum in a graphite crucible. Following the procedure described in the foregoing Example 1, into the furnace there are charged, in succession, 474.0 g of nickel, 5.0 g of molybdenum, 20.0 g of chromium and 1.00 g of palladium.

The resulting alloy has the following composition, percent by weight: 47.4 of Ni, 2.0 of Cr. 0.5 of Mo, 0.1 of Pd, 50.0 of Al.

The catalyst made of this alloy features an activity which is 1.3 to 1.8 times as high as that of the catalysts prepared from alloys Ni-Al-Cr and Ni-Al-Mo.

The catalyst according to the present invention is tested in hydrogenolysis of a Mannich base to agidol under laboratory conditions following the procedure described hereinbelow.

Into a glass reactor comprising a cylindrical vessel (H=700 mm, d=35 mm) provided with a heating means and a stirrer there is charged, under water, 0.84 g of nickel catalyst leached by 10–13% of aluminum (0.5–0.25 mm) fraction containing dopes of Mo, Cr, Pd. Removal of water is effected by heating in a current of hydrogen at the temperature of 120° C. Afterwards into the reactor there is charged a solution of 1.4 g of the Mannich base in 15 ml of decaline.

The stirrer rotating at the speed of 3,000 r.p.m. comprises a hollow pipe with an inlet for hydrogen. Upon stirring, hydrogen is sucked into the stirrer and passed into the solution through the vanes, thus ensuring vigorous agitation of the reaction system.

A sample for chromatographic analysis is taken every 30 minutes. The semi-conversion time which, as a rule, is directly proportional to the reaction rate constant is determined from a plot of relationship of the Mannich base conversion degree vs time.

The final product, i.e. agidol, is a pure white product.

The test results are shown in Table 1 hereinbelow.

Table 1

Comparative characteristics of alloyed catalysts in the reaction of hydrogenolysis of Mannich base (t = 120° C)

| Example No. | Starting alloy, percent by weight | Semi-conversion time, $\tau_{\frac{1}{2}}$ minutes | Catalyst activity (hr.g$^{-1}$) $A = \dfrac{1}{\tau_{\frac{1}{2}} \cdot g}$ | Relative activity, % |
|---|---|---|---|---|
| 1 | 2 | 3 | 4 | 5 |
| 1 | NiAl$_3$-2at.%Mo | 110 | 0.65 | 101 |
| 2 | 38.5%Ni-4%Mo-1.5%Cr-56%Al | 105 | 0.68 | 105 |
| 3 | 39.6%Ni-4%Mo-0.3%Cr-0.1%Pd-56%Al | 92 | 0.78 | 121 |
| 4 | 39.0%Ni-4%Mo-1%Cr-0.03%Pd-56%Al | 78 | 0.93 | 144 |
| 5 | 48%Ni-2%Cr-50%Al | 150 | 0.48 | 74 |
| 6 | 47.0%Ni-2%Cr-0.5%Mo-50%Al | 98 | 0.73 | 113 |
| 7 | 47.4%Ni-2%Cr-0.5%Mo-0.1%Pd-50%Al | 85 | 0.84 | 130 |

To determine the desired product yield and the content of impurities in agidol, the most active catalysts have been tested following the procedure described hereinbelow. Into a glass reactor provided with a Schott filter for a better distribution of hydrogen and a reflux condenser 20 g of an activated catalyst (fraction of 0.5–0.25 mm) are placed.

The reactor is put into a thermostat with the temperature of 120° C, the catalyst is exempted from water by heating in a current of hydrogen and 30 g of a Mannich base are charged thereinto in the form of a 50% solution in decaline. Hydrogen is bubbled through the reaction system at the rate of 25 ml/min. With the residual content of the Mannich base in the reaction system of below 1–2%, hydrogenation of benzene ring is started and the content of impurities in the desired product is increased. In the tests of a catalyst containing, percent by weight: 4 Mo, 0.03 Pd, 0.1 Cr, 39 Ni, 56 Al, a 98% yield of agidol is reached within 75 minutes and the content of stilbenequinone is reduced down to 0.06%. The desired product has a pure white color which is not changed after 6 months storage.

What is claimed is:

1. A catalyst for hydrogenolysis of N,N-dimethyl-3,5-ditert.butyl-4-hydroxybenzylamine comprising an alloy of nickel, aluminum, chromium, molybdenum and palladium; the components being present in the alloy in the following proportions, percent by weight:

nickel — 39.0 to 47.7;
chromium — 0.3 to 2.0;
molybdenum — 0.5 to 4.0;
palladium — 0.01 to 0.20;
aluminum — the balance.

* * * * *